US011866540B2

(12) United States Patent
Kim et al.

(10) Patent No.: US 11,866,540 B2
(45) Date of Patent: Jan. 9, 2024

(54) POLYPROPYLENE RESIN FOR INSULATING ELECTRIC CABLES

(71) Applicant: HANWHA TOTAL PETROCHEMICAL CO., LTD., Seosan-si (KR)

(72) Inventors: BongSeock Kim, Chungcheongnam-do (KR); Youngjoo Lee, Chungcheongnam-do (KR); Youngwook Choi, Chungcheongnam-do (KR); YongSung Chun, Chungcheongnam-do (KR)

(73) Assignee: HANWHA TOTALENERGIES PETROCHEMICAL CO., LTD.

( * ) Notice: Subject to any disclaimer, the term of this patent is extended or adjusted under 35 U.S.C. 154(b) by 854 days.

(21) Appl. No.: 16/960,728

(22) PCT Filed: Nov. 8, 2018

(86) PCT No.: PCT/KR2018/013511
§ 371 (c)(1),
(2) Date: Jul. 8, 2020

(87) PCT Pub. No.: WO2019/143008
PCT Pub. Date: Jul. 25, 2019

(65) Prior Publication Data
US 2020/0339723 A1    Oct. 29, 2020

(30) Foreign Application Priority Data
Jan. 22, 2018   (KR) .................. 10-2018-0007521

(51) Int. Cl.
*C08F 297/08*   (2006.01)
*C07C 69/70*    (2006.01)
(Continued)

(52) U.S. Cl.
CPC ........ *C08F 297/083* (2013.01); *C07C 69/708* (2013.01); *H01B 3/441* (2013.01); *C08F 2500/12* (2013.01); *C08F 2500/17* (2013.01)

(58) Field of Classification Search
CPC ..... C08F 297/083; C08F 210/16; C08L 53/00
See application file for complete search history.

(56) References Cited

U.S. PATENT DOCUMENTS 5,693,729 A   12/1997  Fushimi et al.
6,201,090 B1   3/2001  Sumitomo et al.
(Continued)

FOREIGN PATENT DOCUMENTS

CN   103998476 A   8/2014
CN   108148153 A   6/2018
(Continued)

OTHER PUBLICATIONS

Extended European Search Report for corresponding Application No. 18900740.4 dated Oct. 11, 2021 (8 Pages).
(Continued)

*Primary Examiner* — Catherine S Branch
(74) *Attorney, Agent, or Firm* — Harness, Dickey & Pierce, P.L.C.

(57) ABSTRACT

An ethylene-propylene block copolymer resin is provided that is suitable as an insulation layer of an electric power cable. The ethylene-propylene block copolymer is obtained by polymerization of a propylene homopolymer or an ethylene-propylene random copolymer with an ethylene-propylene rubber copolymer in stages in reactors in the presence of a Ziegler-Natta catalyst obtained using two internal electron donors, wherein one of the two internal electron donors is a compound comprising an ester group and an alkoxy group, the ethylene-propylene block copolymer has a melting temperature of 150 to 160° C., the content of the
(Continued)

solvent extract thereof when extracted at room temperature with xylene is 30 to 50% by weight, and the intrinsic viscosity of the solvent extract is 1.5 to 3.0 dl/g.

11 Claims, 2 Drawing Sheets

(51) Int. Cl.
*C08F 210/16* (2006.01)
*C08L 53/00* (2006.01)
*C07C 69/708* (2006.01)
*H01B 3/44* (2006.01)

(56) References Cited

U.S. PATENT DOCUMENTS

| | | | |
|---|---|---|---|
| 9,593,172 | B2 | 3/2017 | Bantu et al. |
| 9,790,299 | B2 | 10/2017 | Thakare et al. |
| 2014/0255692 | A1 | 9/2014 | Perego |
| 2015/0152199 | A1 | 6/2015 | Bantu et al. |
| 2015/0266982 | A1 | 9/2015 | Thakare et al. |
| 2016/0347880 | A1 | 12/2016 | Bantu et al. |

FOREIGN PATENT DOCUMENTS

| | | |
|---|---|---|
| EP | 2557096 A1 | 2/2013 |
| JP | H09-316283 A | 12/1997 |
| KR | 10-2003-0025392 A | 3/2003 |
| KR | 10-0572616 B1 | 4/2006 |
| KR | 10-2013-0132551 A | 12/2013 |
| KR | 10-2014-0053204 A | 5/2014 |
| KR | 10-2014-0102407 A | 8/2014 |
| KR | 10-2015-0034768 A | 4/2015 |
| KR | 10-2015-0083868 A | 7/2015 |
| KR | 10-2015-0145016 A | 12/2015 |
| KR | 10-1598715 B1 | 2/2016 |
| KR | 2016-0039405 A | 4/2016 |
| KR | 2016-0061788 A | 6/2016 |
| KR | 2016-0149146 A | 12/2016 |
| KR | 10-1795317 B1 | 11/2017 |
| KR | 10-1836008 B1 | 3/2018 |
| WO | 99-065965 A1 | 12/1999 |
| WO | 2013-092624 A1 | 6/2013 |
| WO | 2014-075973 A1 | 5/2014 |
| WO | 2018-001949 A1 | 1/2018 |

OTHER PUBLICATIONS

Japanese Office Action for corresponding Application No. JP 2020-539725 dated Jul. 6, 2021 with English translation (8 Pages).
First Office Action issued in corresponding Chinese Patent Application No. 201880087147.5 dated Aug. 16, 2022, with English translation (20 Pages).

POLYPROPYLENE RESIN FOR INSULATING ELECTRIC CABLES

CROSS REFERENCE TO RELATED APPLICATIONS

This application is a U.S. National Phase application of International Application No. PCT/KR2018/013511, filed on Nov. 8, 2018, and claims priority to Korean Patent Application No. 10-2018-0007521, filed on Jan. 22, 2018. The entire disclosures of the above applications are expressly incorporated by reference herein.

BACKGROUND

Technical Field

The present invention relates to a polypropylene resin suitable for insulating electric power cables. More specifically, the present invention relates to a non-crosslinked polypropylene resin that is excellent in mechanical properties and is recyclable. It relates to an ethylene-propylene block copolymer resin suitable as an insulation layer of an electric power cable, which is excellent in flexibility, heat deformation, and low-temperature impact resistance characteristics and is good in dielectric breakdown strength. The ethylene-propylene block copolymer resin according to the present invention has excellent production stability during polymerization since the polypropylene powders are excellent in flowability although the resin has a high content of a rubber polymer.

Related Art

As a material for insulation layers of common electric power cables, a polyethylene, an ethylene-propylene rubber copolymer (EPR), an ethylene-propylene-diene rubber copolymer (EPDM), or the like is used as crosslinked in order to maintain the mechanical and electrical characteristics at the operating temperature (90 to 110° C.) of high-voltage cables.

However, it is difficult for crosslinked polymers such as crosslinked polyethylene (XLPE) to be recycled when they are defective or have reached their service lives. Since they must be incinerated, they are not environmentally friendly. On the other hand, high-density polyethylene (HDPE), linear low-density polyethylene (LLDPE), and low-density polyethylene (LDPE) in a non-crosslinked form can be recycled. But they have low thermal resistance, whereby they are deformed and melted at high temperatures, making it difficult to be used for high-voltage cables operated at high temperatures.

In recent years, many studies have been conducted on polypropylene, which is a material having a melting temperature of 130° C. or higher with higher thermal resistance than that of polyethylene, so that it can raise the operating temperature of electric power cables to 110° C., and which is recyclable since it is not crosslinked. For example, Korean Laid-open Patent Publication No. 2014-0102407 discloses a technique on an insulation layer of electric power cables having improved insulation characteristics and being recyclable by adding an insulation fluid to polypropylene. Korean Laid-open Patent Publication No. 2014-0053204 discloses an electric power cable that employs an insulation layer comprising a polypropylene resin with an organic nucleating agent to reduce the crystal size.

However, since rubber is additionally compounded in order to resolve the problem of low flexibility caused by the high rigidity of polypropylene, the physical properties may be partially deteriorated due to nonhomogeneous compounding. The organic nucleating agent added to reduce the crystal size causes a cost increase and adverse effects. Thus, the use of polypropylene in an insulation layer of electric power cables is in need of improvement.

In addition, the products generally called RTPO (reactor made thermoplastic olefin) among polypropylene have high flexibility by virtue of the high content of rubber polymerized in the reactor. But as the rubber content increases, the production stability is reduced due to the stickiness of the powders in the polymerization step, impairing the stable continuous production. Thus, it is in need of improvement.

An object of the present invention is to provide a polypropylene resin for solving the above-mentioned problems. In particular, it aims to provide an ethylene-propylene block copolymer resin suitable for insulating electric power cables, which has excellent production stability during polymerization since the polypropylene powders are excellent in flowability although the resin has a high content of rubber polymer, and which is excellent in flexibility, heat deformation, low-temperature impact resistance characteristics, and dielectric breakdown strength.

SUMMARY

According to an embodiment of the present invention to achieve the above object, there is provided an ethylene-propylene block copolymer obtained by polymerization of a propylene homopolymer or an ethylene-propylene random copolymer with an ethylene-propylene rubber copolymer in stages in reactors in the presence of a Ziegler-Natta catalyst obtained using an internal electron donor composed of a combination of a non-aromatic alkoxy ester-based compound and a phthalic acid ester-based compound, wherein the ethylene-propylene block copolymer has a melting temperature (Tm) of 150 to 160° C., the content of the solvent extract when it is extracted at room temperature with xylene is 30 to 50% by weight, and the intrinsic viscosity of the solvent extract is 1.5 to 3.0 dl/g.

Preferably, the Ziegler-Natta catalyst is prepared by reacting a dialkoxy magnesium with a titanium compound in the presence of an organic solvent, and then reacting the resultant with an internal electron donor composed of a combination of a non-aromatic alkoxy ester-based compound and a phthalic acid ester-based compound.

Preferably, the non-aromatic alkoxy ester-based compound comprises a compound represented by the following Formula 1:

Formula 1

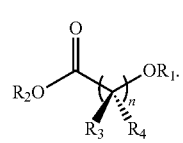

In the above formula, n is 1 to 6, and $R_1$, $R_2$, $R_3$, and $R_4$ are identically or each independently a linear alkyl group having 1 to 12 carbon atoms, a branched alkyl group having 3 to 12 carbon atoms, a vinyl group, a linear or branched alkenyl group having 3 to 12 carbon atoms, a linear alkyl group having 1 to 12 carbon atoms substituted with halogen, a branched alkyl group having 3 to 12 carbon atoms substituted with halogen, a linear or branched alkenyl group having 3 to 12 carbon atoms substituted with halogen, a cycloalkyl group having 3 to 12 carbon atoms, a cycloalkenyl group having 3 to 12 carbon atoms, a cycloalkyl group having 3 to 12 carbon atoms substituted with halogen, or a cycloalkenyl group having 3 to 12 carbon atoms substituted with halogen.

Preferably, the phthalic acid ester-based compound is a benzene-1,2-dicarboxylate compound.

Preferably, triethylaluminum as a co-catalyst and a dicyclopentyldimethoxysilane as an external electron donor are used with the catalyst during the polymerization.

Preferably, when the ethylene-propylene block copolymer resin of the present invention is extracted with xylene at room temperature, the intrinsic viscosity of the solvent insoluble is 2.0 to 4.0 dl/g.

Preferably, the ratio of intrinsic viscosities between the solvent extract and the solvent insoluble (i.e., (intrinsic viscosity of the solvent extract)/(intrinsic viscosity of the solvent insoluble)) is 0.5 to 1.0.

Preferably, the melt index of the ethylene-propylene block copolymer of the present invention is 0.2 to 3.0 g/10 minutes.

Preferably, the ethylene-propylene block copolymer resin of the present invention comprises at least one additive selected from the group consisting of an antioxidant and a neutralizing agent.

Preferably, the content of the additive is 0.2 to 1.0% by weight based on the total weight of the ethylene-propylene block copolymer resin.

According to another embodiment of the present invention, there is provided an electric power cable comprising an insulation layer prepared from the ethylene-propylene block copolymer resin of the present invention.

Effects of the Invention

The ethylene-propylene block copolymer resin according to the present invention has excellent production stability during polymerization and is excellent in flexibility, low-temperature impact resistance, heat deformation, and dielectric breakdown characteristics. Thus, if it is used as a material for an insulation layer of electric power cables, it can have excellent performance.

DETAILED DESCRIPTION

Figure 1:
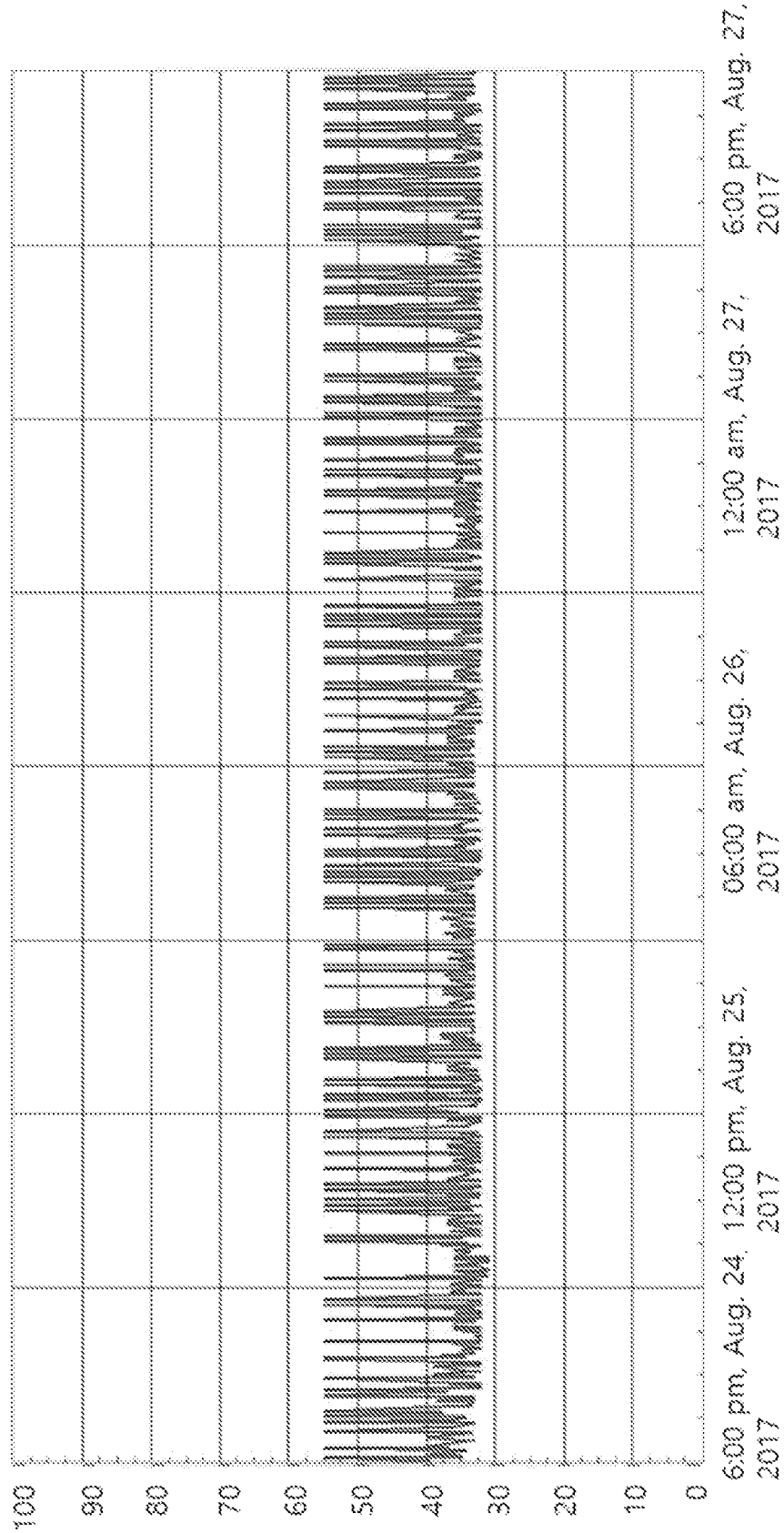
FIG. 1 is a graph showing the tendency that polypropylene powders are discharged from the reactor in the polymerization process of Example 1.

Hereinafter, the present invention will be described in more detail.

The ethylene-propylene block copolymer resin according to an embodiment of the present invention is obtained by polymerization of a propylene homopolymer or an ethylene-propylene random copolymer with an ethylene-propylene rubber copolymer in stages in reactors in the presence of a Ziegler-Natta catalyst obtained using an internal electron donor composed of a combination of a non-aromatic alkoxy ester-based compound and a phthalic acid ester-based compound, wherein the ethylene-propylene block copolymer has a melting temperature (Tm) of 150 to 160° C., the content of the solvent extract when it is extracted at room temperature with xylene is 30 to 50% by weight, and the intrinsic viscosity of the solvent extract is 1.5 to 3.0 dl/g.

The ethylene-propylene block copolymer of the present invention has a melting temperature (Tm) of 150 to 160° C. If the melting temperature is lower than 150° C., the thermal resistance is not sufficient, resulting in high heat deformation. Thus, it is not suitable for a high-voltage electric power cable operated at high temperatures. If the melting temperature exceeds 160° C., the flexibility is deteriorated. Thus, it is not suitable for thick, high-voltage electric power cables that require bending for being laid.

When the ethylene-propylene block copolymer resin of the present invention is extracted at room temperature with xylene, the content of the solvent extract (i.e., rubber component) is 30 to 50% by weight. If the content of the rubber component is less than 30% by weight, the flexibility is insufficient, resulting in deterioration in the low-temperature impact resistance. If the content of the rubber component exceeds 50% by weight, the heat deformation rate is high, whereby it is not suitable for high-voltage electric power cables operated at high temperatures, and the process stability is impaired due to the stickiness of the polypropylene powders in the polymerization process, which is undesirable.

When the ethylene-propylene block copolymer resin of the present invention is extracted at room temperature with xylene, the intrinsic viscosity of the solvent extract (i.e., rubber component) is 1.5 to 3.0 dl/g. If the intrinsic viscosity exceeds 3.0 dl/g, the dispersed phase may agglomerate, whereby when a physical impact is applied, the force is concentrated, resulting in deterioration in the low-temperature impact resistance. If the intrinsic viscosity is less than 1.5 dl/g, the process stability is impaired due to the stickiness of the polypropylene powders caused by the rubber component having a low molecular weight in the polymerization process, which is undesirable.

Meanwhile, when the ethylene-propylene block copolymer resin of the present invention is extracted with xylene at room temperature, the intrinsic viscosity of the solvent insoluble is 2.0 to 4.0 dl/g. In addition, in the ethylene-propylene block copolymer resin of the present invention, the ratio of intrinsic viscosities between the solvent extract and the solvent insoluble (i.e., (intrinsic viscosity of the solvent extract)/(intrinsic viscosity of the solvent insoluble)) is 0.5 to 1.0. If the intrinsic viscosity ratio exceeds 1.0, the dispersed rubber phase may agglomerate, resulting in deterioration in the low-temperature impact resistance, and bend whitening occurs as the dispersed rubber phase grows. If the intrinsic viscosity ratio is less than 0.5, the dispersed rubber phase is finely dispersed, so that it is not suitable for absorbing physical impacts, resulting in deterioration in the low-temperature impact resistance. Thus, it is not suitable for electric power cables.

In addition, the melt index of the ethylene-propylene block copolymer resin of the present invention is 0.2 to 3.0 g/10 minutes. If the melt index is less than 0.2 g/10 minutes, the load during extrusion rises and melt fracture occurs due to the high melt pressure, resulting in a reduction in the productivity. If the melt index exceeds 3.0 g/10 minutes, a deflection occurs during extrusion, which is not preferable since the thickness uniformity is deteriorated.

The ethylene-propylene block copolymer resin of the present invention is obtained by polymerization of a propylene homopolymer or an ethylene-propylene random copolymer with an ethylene-propylene rubber copolymer in stages in reactors in the presence of a Ziegler-Natta catalyst.

There is no particular limitation to the method of preparing the ethylene-propylene block copolymer. Any method of preparing an ethylene-propylene block copolymer known in the art to which the present invention pertains may be used as it is or as appropriately modified.

Preferably, the ethylene-propylene block copolymer resin may be prepared by a polymerization method known to those skilled in the art using Mitsui's Hypol process in which two bulk reactors and two gas-phase reactors are connected in series, and polymerization is continuously carried out therein.

Specifically, in the first- to third-stage reactors, propylene alone is injected to produce a propylene homopolymer, or ethylene is additionally injected thereto to produce an ethylene-propylene random copolymer. In the polymerization of the ethylene-propylene random copolymer, the same amount of ethylene may be copolymerized in each polymerization reactor. In the ensuing fourth-stage reactor, ethylene and propylene may be injected to polymerize an ethylene-propylene rubber, thereby obtaining the final ethylene-propylene block copolymer. The melt index of the resulting copolymer can be controlled by injecting hydrogen into each reactor.

The Ziegler-Natta catalyst used in the polymerization step is obtained using an internal electron donor composed of a combination of a non-aromatic alkoxy ester-based compound and a phthalic acid ester-based compound. Specifically, the Ziegler-Natta catalyst used in the polymerization step is prepared by reacting a dialkoxy magnesium with a titanium compound in the presence of an organic solvent, and then reacting the resultant with an internal electron donor composed of a combination of a non-aromatic alkoxy ester-based compound and a phthalic acid ester-based compound.

Preferably, the non-aromatic alkoxy ester-based compound comprises a compound represented by the following Formula 1:

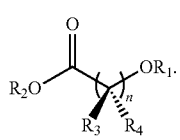

Formula 1

In the above formula, n is 1 to 6, and $R_1$, $R_2$, $R_3$, and $R_4$ are identically or each independently a linear alkyl group having 1 to 12 carbon atoms, a branched alkyl group having 3 to 12 carbon atoms, a vinyl group, a linear or branched alkenyl group having 3 to 12 carbon atoms, a linear alkyl group having 1 to 12 carbon atoms substituted with halogen, a branched alkyl group having 3 to 12 carbon atoms substituted with halogen, a linear or branched alkenyl group having 3 to 12 carbon atoms substituted with halogen, a cycloalkyl group having 3 to 12 carbon atoms, a cycloalkenyl group having 3 to 12 carbon atoms, a cycloalkyl group having 3 to 12 carbon atoms substituted with halogen, or a cycloalkenyl group having 3 to 12 carbon atoms substituted with halogen.

In addition, the phthalic acid ester-based compound used in the preparation of the Ziegler-Natta catalyst used in the polymerization step is preferably a benzene-1,2-dicarboxylate compound.

Details of the raw materials, production methods, and the like for obtaining the Ziegler-Natta catalyst used in the preparation of the ethylene-propylene block copolymer resin of the present invention are disclosed in Korean Patent Application No. 2016-0164086 filed by the present applicant.

It is preferable to use an organoaluminum compound (e.g., triethylaluminum) as a co-catalyst and a dialkyldialkoxysilane-based compound (e.g., dicyclopentyldimethoxysilane) as an external electron donor with the Ziegler-Natta catalyst in the polymerization step.

The ethylene-propylene block copolymer resin of the present invention may further comprise such an additive as an antioxidant, a neutralizing agent, and the like within a range that does not contradict the gist of the present invention.

For example, pentaerythritol tetrakis(3,5-di-t-butyl-4-hydroxyhydrocinnamate; Irganox 1010) manufactured by BASF may be used as an antioxidant, and calcium stearate (SC-110) manufactured by Songwon may be used as a neutralizing agent for removing any catalyst residue. But they are not limited thereto.

Preferably, the content of the additive may be 0.2 to 1.0% by weight based on the total weight of the polyolefin resin composition.

According to another embodiment of the present invention, there is provided an electric power cable comprising an insulation layer prepared from the ethylene-propylene block copolymer resin of the present invention.

The method for forming the insulation layer of an electric power cable from the ethylene-propylene block copolymer resin of the present invention is not particularly limited.

EXAMPLES

Hereinafter, the present invention is explained in detail with reference to the following examples and comparative examples. However, the following examples are intended to further illustrate the present invention. The scope of the present invention is not limited thereto only.

Examples 1 to 4

A 1-liter glass reactor equipped with a stirrer was sufficiently purged with nitrogen and then charged with 112 ml of toluene and 15 g of diethoxy magnesium (in a spherical shape having an average particle diameter of 20 μm, a particle size distribution index of 0.86, and an apparent density of 0.35 g/ml). While the mixture was maintained at 10° C., 20 ml of titanium tetrachloride diluted in 30 ml of toluene was added thereto over 1 hour. Then, while the temperature of the reactor was raised to 100° C., a mixture of 3.6 g of diisobutyl phthalate and 1.4 g of methyl 4-methoxybutanoate was injected thereto. After it was maintained at 100° C. for 2 hours, the temperature was lowered to 90° C., and stirring was stopped. The supernatant was removed, followed by washing once with 200 ml of toluene. Added thereto were 120 ml of toluene and 20 ml of titanium tetrachloride. The temperature was then raised to 100° C. and maintained for 2 hours. This procedure was repeated once again. The slurry mixture upon the aging procedure was washed twice with 200 ml of toluene each time and 5 times with 200 ml of normal hexane each time at 40° C., thereby obtaining a light-yellow solid catalyst component. It was dried in a flow of nitrogen for 18 hours to obtain a catalyst. Triethyl aluminum was used as a co-catalyst, and dicyclopentyl dimethoxysilane was used as an external electron donor.

An ethylene-propylene block copolymer was prepared in the presence of the catalyst thus prepared in the Hypol process. Here, the operating temperatures and pressures of the bulk reactors as the first- and second-stage reactors were in the range of 68 to 75° C. and 30 to 40 kg/cm$^2$, and 68 to 75° C. and 25 to 35 kg/cm$^2$, respectively. The operating temperatures and pressures of the gas-phase reactors as the third- and fourth-stage reactors were in the range of 75 to 82° C. and 15 to 20 kg/cm$^2$, and 68 to 75° C. and 10 to 17 kg/cm$^2$, respectively. In the first- to third-stage reactors, propylene alone was injected to produce a propylene homopolymer, or ethylene was additionally injected thereto to produce an ethylene-propylene random copolymer. In the polymerization of the ethylene-propylene random copolymer, the same amount of ethylene was copolymerized in each polymerization reactor. Here, ethylene was copolymerized so that the melting temperature was shown in Table 1. In the ensuing fourth-stage reactor, ethylene and propylene were injected to polymerize an ethylene-propylene rubber, thereby obtaining the final ethylene-propylene block copolymer. The melt index was controlled by injecting hydrogen into each reactor. According to the method as described above, the ethylene-propylene block copolymer was polymerized as shown in Table 1 below.

Comparative Examples 1 to 5

The polymerization was carried out in the same manner as in Examples 1 to 4, except that diisobutyl phthalate was used as an internal electron donor for the catalyst.

Comparative Example 6

A crosslinked polyethylene (Hanwha Chemical, CLNB-8141S), which is commercially available for electric power cables, was used.

The physical properties of the compositions prepared in the Examples and the Comparative Examples were measured according to the following methods and standards. The results are shown in Tables 1 and 2 below.

(1) Melt Index

Melt index was measured at 230° C. under a load of 2.16 kg according to the ASTM D 1238 method.

(2) Melting Temperature

A sample was kept isothermal at 200° C. for 10 minutes in a differential scanning calorimeter (DSC; Q2000, TA Instrument) to remove the thermal history and then cooled from 200° C. to 30° C. at a rate of 10° C. per minute for crystallization thereof to impart the same thermal history. Then, the sample was kept isothermal at 30° C. for 10 minutes, followed by heating the sample at a rate of 10° C. per minute. The melting temperature (Tm) was obtained from the peak temperature.

(3) Content of a Solvent Extract (or Xylene Soluble)

A polypropylene resin was dissolved in xylene at a concentration of 1% at 140° C. for 1 hour and left at room temperature for 2 hours for extraction. The weight of the extract was measured and expressed in percent based on the total weight of the polypropylene resin.

(4) Intrinsic Viscosity

Intrinsic viscosity of a sample was measured in a decalin solvent at 135° C. using a viscometer.

(5) Flowability of Powders 40 g of polypropylene powders was filled in a funnel (having an angle 53° and an outlet diameter of 10 mm), and the time for the powders to come out was measured.

(6) Dischargeability of Powders

Figure 2:
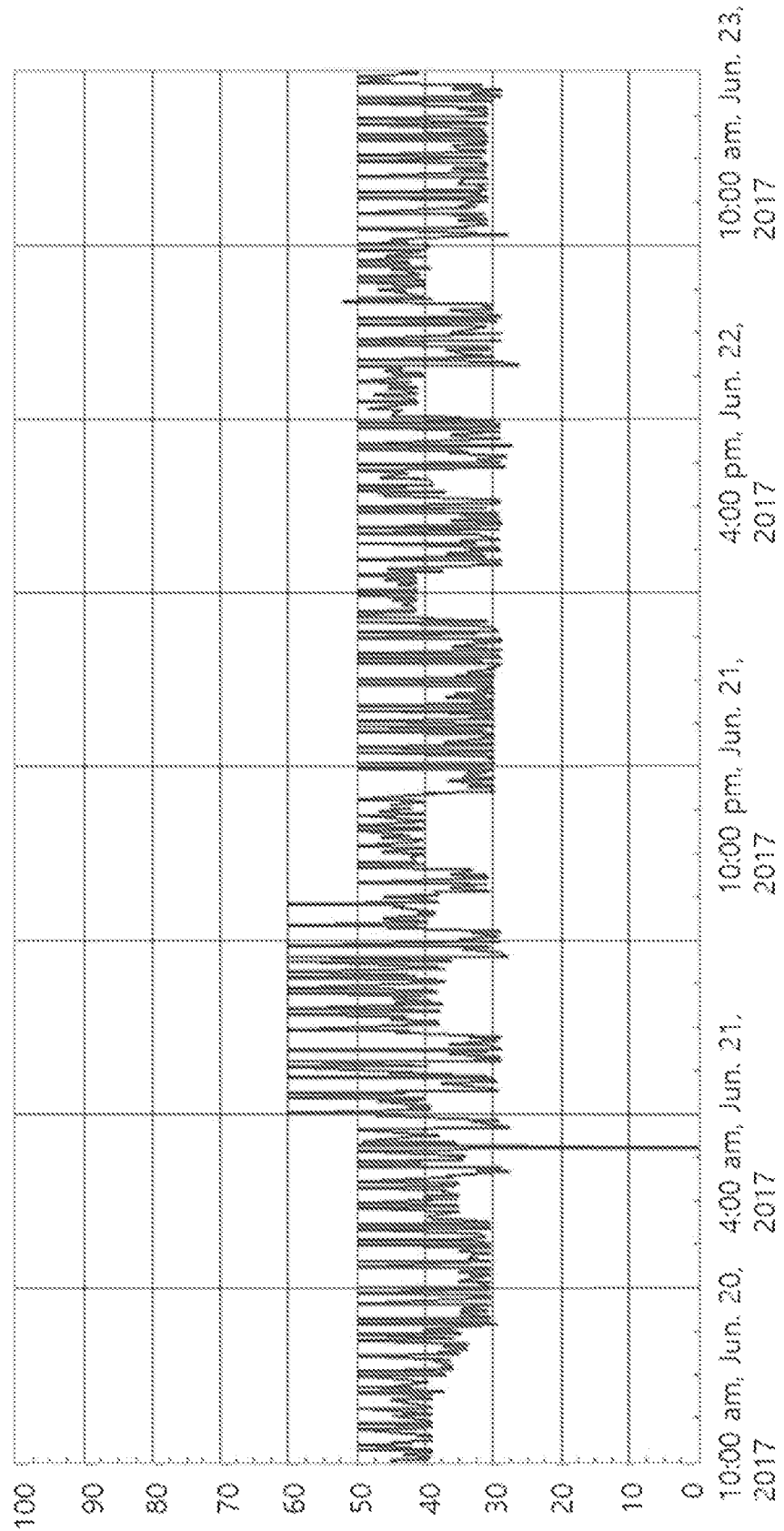
FIG. 2 is a graph showing the tendency that polypropylene powders are discharged from the reactor in the polymerization process of Comparative Example 1.

Dischargeability of the polymerized powders in the polypropylene polymerization process was qualitatively compared. The dischargeability was compared by checking the tendency that the polypropylene powders were discharged from the reactor as shown in FIG. 1 or 2.

(7) Flexural Modulus (FM)

Flexural modulus was measured in accordance with the ASTM D 790 method.

(8) Brittleness Temperature Test

Specimens having a length of 38 mm, a width of 6 mm, and a thickness of 2 mm were obtained by injection molding at 240° C. Five specimens were subjected to the brittleness temperature test −40° C. in accordance with the KS C 3004 method to check the number of specimens broken.

(9) Heat Deformation

A specimen having a length of 30 mm, a width of 15 mm, and a thickness of 2 mm was prepared by injection molding at 240° C. According to the KS C IEC 60811-508 method, a load of 1.6 kg was applied to the specimen at 130° C. for 6 hours, and the deformed thickness was measured. The deformation ratio was obtained by dividing the deformed thickness by the initial thickness.

(10) Whitening Resistance

A specimen for flexural modulus test was bent at 90°, and the degree of whitening was visually observed (○: excellent, Δ: good, ×: poor).

(11) Alternating Current Breakdown Voltage

Polypropylene was pressed at 200° C. using a press into a sheet having a thickness of 1 mm and then cooled to room temperature, thereby preparing a polypropylene specimen. A crosslinked polyethylene (XLPE) specimen having a thickness of 1 mm was prepared by press molding at 180° C. Alternating current breakdown voltage was measured at room temperature using hemisphere electrodes having a diameter of 12.7 mm and plate electrodes according to the ASTM D 149-92 method.

TABLE 1

| | | Example | | | | Comparative Example | | | | |
|---|---|---|---|---|---|---|---|---|---|---|
| | | 1 | 2 | 3 | 4 | 1 | 2 | 3 | 4 | 5 |
| Resin characteristic | Melt index (g/10 min) | 0.8 | 0.5 | 0.7 | 1.0 | 1.8 | 0.6 | 0.8 | 1.6 | 1.8 |
| | Melting temp. (Tm; ° C.) | 152 | 159 | 151 | 150 | 151 | 151 | 150 | 164 | 145 |
| | Solvent extract content (wt. %) | 40 | 48 | 35 | 32 | 36 | 38 | 26 | 55 | 35 |
| | Intrinsic viscosity of solvent insoluble (dl/g) | 3.4 | 3.1 | 3.1 | 2.5 | 3.1 | 2.5 | 2.7 | 3.1 | 2.0 |
| | Intrinsic viscosity of solvent extract (dl/g) | 1.7 | 2.9 | 2.2 | 2.5 | 1.2 | 3.5 | 2.5 | 2.8 | 2.4 |

TABLE 1-continued

| | | Example | | | | Comparative Example | | | | |
|---|---|---|---|---|---|---|---|---|---|---|
| | | 1 | 2 | 3 | 4 | 1 | 2 | 3 | 4 | 5 |
| | Ratio of intrinsic viscosities* | 0.5 | 0.9 | 0.7 | 1.0 | 0.4 | 1.4 | 0.9 | 0.9 | 1.2 |
| Process characteristic | Flowability of powders (sec) | 9.0 | 9.6 | 7.5 | 7.3 | 28 | 7.4 | 6.8 | 24 | 7.7 |
| | Dischargeability of powders | Good | Good | Good | Good | Poor | Good | Good | Poor | Good |
| Physical property | Flexural modulus (kgf/cm²) | 4000 | 3500 | 4500 | 4700 | 4500 | 4300 | 5400 | 5000 | 4000 |
| | Brittleness temp. test (ea) | 0 | 0 | 0 | 0 | 2 | 1 | 1 | 0 | 0 |
| | Heat deformation (%) | 28 | 34 | 20 | 19 | 26 | 25 | 10 | 55 | 52 |
| | Whitening resistance | ○ | ○ | ○ | ○ | ○ | x | ○ | ○ | Δ |

*Ratio of intrinsic viscosities = (intrinsic viscosity of the solvent extract)/(intrinsic viscosity of the solvent insoluble)

As can be seen from Table 1 and FIG. 1, the polypropylene resin of the present invention had good flowability and dischargeability of powders in the polymerization process, had a low flexural modulus as a barometer of flexibility, and was excellent in low-temperature impact resistance, heat deformation, and bend whitening.

In contrast, in Comparative Example 1, the intrinsic viscosity of the solvent extract was low, so that the flowability of powders was not good. As can be seen from FIG. 2, the discharge of powders from the reactor was irregular, so that the process stability was not good, and the intrinsic viscosity ratio was low, resulting in deterioration in the low-temperature impact resistance. In Comparative Example 2, the intrinsic viscosity of the solvent extract and the intrinsic viscosity ratio were high, resulting in deterioration in the low-temperature impact resistance and whitening resistance. In Comparative Examples 3 and 4, the content of the solvent extract was low and the melting temperature was high, resulting in insufficient flexibility, and the low-temperature impact resistance or heat deformation was not good, respectively. In particular, in Comparative Example 4, the content of the solvent extract was high, so that the flowability and dischargeability of powders were not good. In Comparative Example 5, since the melting temperature was low and the intrinsic viscosity ratio was high, the heat deformation and bend whitening were not good.

TABLE 2

| | Example 1 | Comparative Example 6 |
|---|---|---|
| Resin type | Polypropylene | Crosslinked polyethylene |
| Alternating current breakdown voltage (kV) | 39 | 35 |

As can be seen from Table 2, the polypropylene resin obtained in Example 1 had a good alternating current breakdown voltage as compared with that of the crosslinked polyethylene currently used commercially in electric power cables.

INDUSTRIAL APPLICABILITY

The ethylene-propylene block copolymer resin according to the present invention has excellent production stability during polymerization and is excellent in flexibility, low-temperature impact resistance, heat deformation, and dielectric breakdown characteristics. Thus, if it is used as a material for an insulation layer of electric power cables, it can have excellent performance.

The invention claimed is:

1. An ethylene-propylene block copolymer resin obtained by polymerization of a propylene homopolymer or an ethylene-propylene random copolymer with an ethylene-propylene rubber copolymer in stages in reactors in the presence of a Ziegler-Natta catalyst obtained comprising an internal electron donor composed of a combination of a non-aromatic alkoxy ester-based compound and a phthalic acid ester-based compound, wherein the ethylene-propylene block copolymer resin has a melting temperature (Tm) of 150 to 160° C., the content of the solvent extract when it is extracted at room temperature with xylene is 30 to 50% by weight, and the intrinsic viscosity of the solvent extract is 1.5 to 3.0 dl/g.

2. The ethylene-propylene block copolymer resin of claim 1, wherein the Ziegler-Natta catalyst is prepared by reacting a dialkoxy magnesium with a titanium compound in the presence of an organic solvent, and then reacting the resultant product with the internal electron donor composed of a combination of a non-aromatic alkoxy ester-based compound and a phthalic acid ester-based compound.

3. The ethylene-propylene block copolymer resin of claim 1, wherein the non-aromatic alkoxy ester-based compound comprises a compound represented by the following Formula 1:

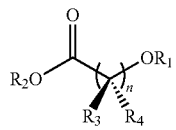

Formula 1 in the above formula, n is 1 to 6, and $R_1$, $R_2$, $R_3$, and $R_4$ are identically or each independently a linear alkyl group having 1 to 12 carbon atoms, a branched alkyl group having 3 to 12 carbon atoms, a vinyl group, a linear or branched alkenyl group having 3 to 12 carbon atoms, a linear alkyl group having 1 to 12 carbon atoms substituted with halogen, a branched alkyl group having 3 to 12 carbon atoms substituted with halogen, a linear or branched alkenyl group having 3 to 12 carbon atoms substituted with halogen, a cycloalkyl group having 3 to 12 carbon atoms, a cycloalkenyl group having 3 to 12 carbon atoms, a cycloalkyl group having 3 to 12 carbon atoms substituted with halogen, or a cycloalkenyl group having 3 to 12 carbon atoms substituted with halogen.

4. The ethylene-propylene block copolymer resin of claim 1, wherein the phthalic acid ester-based compound is a benzene-1,2-dicarboxylate compound.

5. The ethylene-propylene block copolymer resin of claim 1, wherein triethylaluminum as a co-catalyst and a dicyclopentyldimethoxysilane as an external electron donor are used as mixed with the catalyst during the polymerization.

6. The ethylene-propylene block copolymer resin of claim 1, wherein when the ethylene-propylene block copolymer resin is extracted with xylene at room temperature, the intrinsic viscosity of the solvent insoluble is 2.0 to 4.0 dl/g.

7. The ethylene-propylene block copolymer resin of claim 6, wherein the ratio of intrinsic viscosities between the solvent extract and the solvent insoluble (i.e., (intrinsic viscosity of the solvent extract)/(intrinsic viscosity of the solvent insoluble)) is 0.5 to 1.0.

8. The ethylene-propylene block copolymer resin of claim 1, which has a melt index of 0.2 to 3.0 g/10 minutes.

9. The ethylene-propylene block copolymer resin of claim 1, which further comprises at least one additive selected from the group consisting of an antioxidant and a neutralizing agent.

10. The ethylene-propylene block copolymer resin of claim 9, wherein the content of the additive is 0.2 to 1.0% by weight based on the total weight of the ethylene-propylene block copolymer resin.

11. An electric power cable comprising an insulation layer, wherein the insulation layer comprises the ethylene-propylene block copolymer of claim 1.

* * * * *